US008444551B2

(12) United States Patent
Adams et al.

(10) Patent No.: US 8,444,551 B2
(45) Date of Patent: *May 21, 2013

(54) CONTROLLABLE ENDOSCOPIC SHEATH APPARATUS AND RELATED METHOD OF USE

(75) Inventors: Ronald Adams, Holliston, MA (US); Michael Banik, Bolton, MA (US); Charles Pugsley, Pelham, NH (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/092,353

(22) Filed: Apr. 22, 2011

(65) Prior Publication Data

US 2011/0257479 A1 Oct. 20, 2011

Related U.S. Application Data

(63) Continuation of application No. 11/415,418, filed on May 2, 2006, now Pat. No. 7,951,072, which is a continuation of application No. 10/724,740, filed on Dec. 2, 2003, now Pat. No. 7,070,559, which is a continuation of application No. 09/725,814, filed on Nov. 30, 2000, now Pat. No. 6,761,685, which is a continuation of application No. 09/267,109, filed on Mar. 12, 1999, now Pat. No. 6,179,776.

(51) Int. Cl.
*A61B 1/00* (2006.01)
(52) U.S. Cl.
USPC ........... 600/121; 600/114; 600/143; 600/144; 600/146
(58) Field of Classification Search
USPC ................ 600/104, 106–107, 121–125, 143, 600/153
See application file for complete search history.

(56) References Cited

U.S. PATENT DOCUMENTS 3,896,793 A 7/1975 Mitsui et al.
4,245,624 A * 1/1981 Komiya ........................ 600/106
(Continued)

FOREIGN PATENT DOCUMENTS

DE 42 28 459 A1 3/1994
DE 197 49 687 A1 5/1998
(Continued)

OTHER PUBLICATIONS

International Preliminary Examination Report issued in International Application No. PCT/IB00/00251 (Publication No. WO 00/54653); Date of Completion: Apr. 25, 2001.

(Continued)

*Primary Examiner* — Matthew J Kasztejna
(74) *Attorney, Agent, or Firm* — Bookoff McAndrews, PLLC

(57) ABSTRACT

A controllable sheath for optimizing the control of surgical instruments at the operation site includes a flexible sheath surrounding an endoscope and including a lumen extending along the walls of the sheath and adjacent to the endoscope. The lumen permits the passage of surgical instruments from the proximal end of the endoscopic device to the operation site. The lumen extends beyond the distal end of the endoscope and deflects at the distal end as desired by the operator's manipulation of a controller device. This distal end deflection may occur through various different techniques where the ability to deflect the lumen gives the operator increased control and maneuverability over the surgical implements located in the lumen. Depending upon the particular requirements of the surgical procedure, the controllable sheath may include any number of lumens capable of distal end deflection.

24 Claims, 13 Drawing Sheets

U.S. PATENT DOCUMENTS

| | | | |
|---|---|---|---|
| 4,285,376 A | | 8/1981 | Ausnit |
| 4,646,722 A | | 3/1987 | Silverstein et al. |
| 4,676,229 A | | 6/1987 | Krasnicki et al. |
| 4,686,965 A | | 8/1987 | Bonnet et al. |
| 4,697,576 A | | 10/1987 | Krauter |
| 4,741,326 A | | 5/1988 | Sidall et al. |
| 4,793,326 A | | 12/1988 | Shishido |
| 4,886,049 A | | 12/1989 | Darras |
| 5,025,778 A | | 6/1991 | Silverstein et al. |
| 5,100,420 A | | 3/1992 | Green et al. |
| 5,109,830 A | | 5/1992 | Cho |
| 5,171,222 A | | 12/1992 | Euteneuer et al. |
| 5,217,001 A | | 6/1993 | Nakao et al. |
| 5,226,876 A | | 7/1993 | Filipi et al. |
| 5,259,366 A | | 11/1993 | Reydel et al. |
| 5,345,937 A | | 9/1994 | Middleman et al. |
| 5,383,849 A | | 1/1995 | Johlin, Jr. |
| 5,386,818 A | * | 2/1995 | Schneebaum et al. ........ 600/104 |
| 5,423,830 A | * | 6/1995 | Schneebaum et al. ........ 606/115 |
| 5,503,616 A | | 4/1996 | Jones |
| 5,538,497 A | | 7/1996 | Hori |
| 5,607,435 A | | 3/1997 | Sachdeva et al. |
| 5,624,380 A | * | 4/1997 | Takayama et al. ............ 600/146 |
| 5,662,585 A | | 9/1997 | Willis et al. |
| 5,746,692 A | | 5/1998 | Bacich et al. |
| 5,749,828 A | | 5/1998 | Solomon et al. |
| 5,749,889 A | | 5/1998 | Bacich et al. |
| 5,820,546 A | | 10/1998 | Ouchi |
| 5,916,147 A | * | 6/1999 | Boury ........................... 600/146 |
| 5,944,654 A | | 8/1999 | Crawford |
| 5,954,731 A | * | 9/1999 | Yoon ............................. 606/144 |
| 5,984,932 A | * | 11/1999 | Yoon ............................. 606/147 |
| 5,997,547 A | | 12/1999 | Nakao et al. |
| 6,036,636 A | * | 3/2000 | Motoki et al. ................. 600/146 |
| 6,066,090 A | * | 5/2000 | Yoon ............................. 600/113 |
| 6,071,233 A | | 6/2000 | Ishikawa et al. |
| 6,099,464 A | | 8/2000 | Shimizu et al. |
| 6,106,521 A | * | 8/2000 | Blewett et al. .................. 606/41 |
| 6,126,633 A | | 10/2000 | Kaji et al. |
| 6,352,503 B1 | | 3/2002 | Matsui et al. |
| 6,849,042 B2 | | 2/2005 | Christopher |
| 7,029,435 B2 | | 4/2006 | Nakao |
| 7,261,728 B2 | | 8/2007 | Long et al. |
| 7,951,072 B2 | | 5/2011 | Adams et al. |

FOREIGN PATENT DOCUMENTS

| | | |
|---|---|---|
| EP | 0 667 126 A1 | 8/1995 |
| JP | 63-292935 A | 11/1988 |

OTHER PUBLICATIONS

International Search Report issued in International Application No. PCT/IB00/00251 (Publication No. WO 00/54653); Date of Mailing: Jun. 29, 2000.

Written Opinion issued in International Application No. PCT/IB00/00251 (Publication No. WO 00/54653); Date of Mailing: Dec. 22, 2000.

* cited by examiner

CONTROLLABLE ENDOSCOPIC SHEATH APPARATUS AND RELATED METHOD OF USE

This is a continuation of U.S. patent application Ser. No. 11/415,418, filed May 2, 2006 now U.S. Pat. No. 7,951,072, which is a continuation of U.S. patent application Ser. No. 10/724,740, filed Dec. 2, 2003, now U.S. Pat. No. 7,070,559, which is a continuation of U.S. patent application Ser. No. 09/725,814, filed Nov. 30, 2000, now U.S. Pat. No. 6,761,685, which is a continuation of U.S. patent application Ser. No. 09/267,109, filed Mar. 12, 1999, now U.S. Pat. No. 6,179,776, all of which are incorporated herein by reference.

BACKGROUND OF THE INVENTION

1. Field of the Invention

The present invention relates to endoscopic devices, and, more particularly, to a sheath, external to an endoscope, that includes working channels capable of controllable deflection at their distal ends, and to a related method of using the sheath during an endoscopic operation.

2. Background of the Related Art

An endoscope is a flexible medical device for insertion into a body passageway or cavity that enables an operator, positioned at a remote external location, to perform certain surgical procedures at a site internal to the patient's body. In general, an endoscope includes a long flexible tubular member equipped with, for example, a miniature viewing device, an illumination device, and working channels. The endoscope has a proximal end that remains external to the patient and a distal end having an endoscope tip for insertion into a body cavity of the patient.

A typical endoscope 10 is illustrated in FIG. 1. An illumination device of endoscope 10 typically includes a lens 16 at an endoscope tip 14. Lens 16 is positioned proximate to a viewing device 17. Light emanates from lens 16 to enable viewing device 17 to capture images in the in the body cavity and electrically or optically transmit the images through a tubular body 13 of endoscope 10 for display at an external monitor. Once viewing the transmitted images, the endoscope operator may insert one or more surgical instruments through working channels 18, 20 to perform an endoscopic procedure at the internal body cavity site. These endoscopic procedures may include, for example, snare resections, injections, or biopsies of particular internal areas of the patient's body.

Often, these endoscopic procedures require the use of multiple endoscopic instruments working in cooperation, where each instrument inserts through a separate working channel. Because these instruments work in cooperation, their maneuverability at the endoscope tip is critical to the success of the surgical procedure. But, this maneuverability is limited by the diameter constraints of the endoscope tip which, in turn, are dictated by the particular body cavity dimensions of the patient. Endoscope designs have evolved to minimize the diameter of the endoscope tip to limit the discomfort experienced by the patient. These designs, however, have failed to maximize the maneuverability of therapeutic devices at the endoscope tip. For example, the working channel of the conventional endoscope remains coexistent with the endoscope and offers no independent motion in relation to the endoscope. Such a limitation impedes the maneuverability of surgical instruments at the operation site since they are constrained to follow the movement of the endoscope.

With reference once again to FIG. 1, working channels 18, 20 of endoscope 10 are located internal to endoscope 10, positioned in close proximity to one another, and fixed in the endoscope with no independent mobility. In essence, working channels 18, 20 simply provide a passage for the surgical instruments to reach endoscope tip 14. Because working channels 18, 20 are fixed and located in such close proximity to one another, the endoscope operator has limited range of motion over the surgical instruments at the operation site. This limited mobility not only hinders the cooperation between the multiple surgical instruments but also inhibits the potential for advancement into more complex endoscopic procedures.

Consequently, there is a need for an endoscopic device with working channels that, in addition to providing a passage for the surgical instruments, optimizes the mobility of the surgical instruments at the operation site, while maintaining the required dimensional constraints to permit travel of the endoscopic device through the body cavities of the patient.

SUMMARY OF THE INVENTION

The advantages and purpose of the invention will be set forth in part in the description which follows, and in part will be obvious from the description, or may be learned by practice of the invention. The advantages and purpose of the invention will be realized and attained by means of the elements and combinations particularly pointed out in the appended claims.

To attain the advantages and in accordance with the present invention, as embodied and broadly described herein, the controllable endoscopic sheath of the present invention includes a flexible elongated sheath for surrounding an endoscope. The flexible sheath contains a flexible working lumen extending within the sheath and adjacent to the endoscope so as to permit the lumen to move in relation to the endoscope and beyond a distal tip of the endoscope. The flexible working lumen includes a deflectable distal end. The endoscopic sheath also includes a controller device connected to the distal end of the lumen for controlling deflection of the distal end of the lumen.

According to an aspect of the invention, the controller device includes a wire member disposed on the lumen. The wire member possesses a naturally deflected state as well as an elastic memory and returns its deflected elastic memory once the wire member extends beyond a distal tip of the endoscope. The distal end of the lumen deflects in response to the distal end deflection of the wire member.

In another aspect, the controller device includes a stiffening member disposed alongside the outside of the lumen and adjacent to the endoscope. The lumen further includes a deflectable lumen tip having a naturally deflected state and an elastic memory. The material of the stiffening member possesses sufficient rigidity to impede only the elastic memory of the lumen tip. The lumen tip, once extended beyond the stiffening member, returns to its original deflected position, thus, causing the distal end of the lumen to deflect.

In still another aspect of the invention, the controller device includes a flexible extension disposed on the lumen at a distal end. The flexible extension attaches to a flexible elongated member that extends along the lumen from the proximal to the distal end of the lumen. The elongated member eccentrically attaches to the flexible extension. The proximal pulling of the elongated member shortens the corresponding length of the elongated member eccentrically attached to the flexible extension and causes the flexible extension to deflect. In response to this deflection, the distal end of the lumen deflects.

The method for using the controllable endoscopic sheath of the present invention in an endoscopic procedure includes inserting an endoscopic device into a body cavity, the endoscopic device having an endoscope, a flexible elongated sheath surrounding the endoscope, and a flexible lumen extending with the sheath and adjacent to the endoscope for containing a surgical tool. Maneuvering the endoscopic device through the body cavity and proximate to an operation site. Once arriving proximate to the operation site, extending a distal end of the lumen beyond a distal tip of the endoscope. And deflecting the extended distal end of the lumen to maneuver the surgical tool.

According to an aspect of the invention, the endoscopic device further includes a wire member having a naturally deflected state as well as an elastic memory and disposed adjacent to the lumen. For such an endoscopic device, the deflecting step includes extending the wire member beyond the distal tip of the endoscope.

In another aspect, the endoscopic device includes a lumen having a naturally deflected state and elastic memory at the distal end. For such an endoscopic device, the deflecting step includes extending a stiffening member beyond the distal tip of the endoscope, where the stiffening member impedes the distal end of the lumen from retaining its naturally defected state.

In still another aspect of the invention, the endoscopic device includes an elongated member disposed on the lumen and eccentrically attached to a flexible extension. The elongated member extends from a proximal end of the lumen to a point proximate the distal end of the lumen and the flexible extension resides at the distal end of the lumen. For such an endoscopic device, the deflecting step includes retracting the elongated member from the proximal end to shorten the distal end of the elongated member and deflect the flexible extension.

Additional advantages of the invention will be set forth in part in the description which follows, and in part will be obvious from the description, or may be learned by practice of the invention. The advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention. In the drawings.

DESCRIPTION OF THE PREFERRED EMBODIMENTS

Reference will now be made in detail to the present preferred embodiments of the invention, examples of which are illustrated in the accompanying drawings. Wherever possible, the same reference numbers will be used throughout the drawings to refer to the same or like parts.

The present invention is directed towards a controllable sheath for use with an endoscope. The sheath surrounds the endoscope and has a deflectable distal end. The sheath further includes at least one lumen, and preferably a plurality of lumens, extending within the sheath and along the outside of the endoscope. During an operation at a surgical site, endoscopic instruments insert into the lumens to perform a surgical operation. Since the lumens are located along the outside of the endoscope, working channels internal to the endoscope can be eliminated to decrease the diameter of the endoscope. By positioning the lumens along the endoscope exterior, the overall cross-sectional dimension of the endoscopic device may be decreased, thus, optimizing the maneuverability of the endoscopic device through the operative channels of the patient.

The distal end of the lumens, according to the present invention, may be controlled to extend beyond the endoscope tip and deflect by a controller device. The controller device connects to the distal end of the lumen and controls the distal end deflection of the lumen. As such, the sheath optimizes the mobility of the entire device, including the endoscope, through the operative channels. The lumens also increase the maneuverability of the surgical instruments at the operation site by permitting the distal end of the instruments to be directed more closely to the site and move independently with respect to one another in a myriad of directions. To permit this enhanced maneuverability, the lumen is preferably constructed of a flexible plastic material, such as teflon, polypropylene, polytetrafluoroethylene, tetrafluoroethylene, or nylon.

Figure 1:
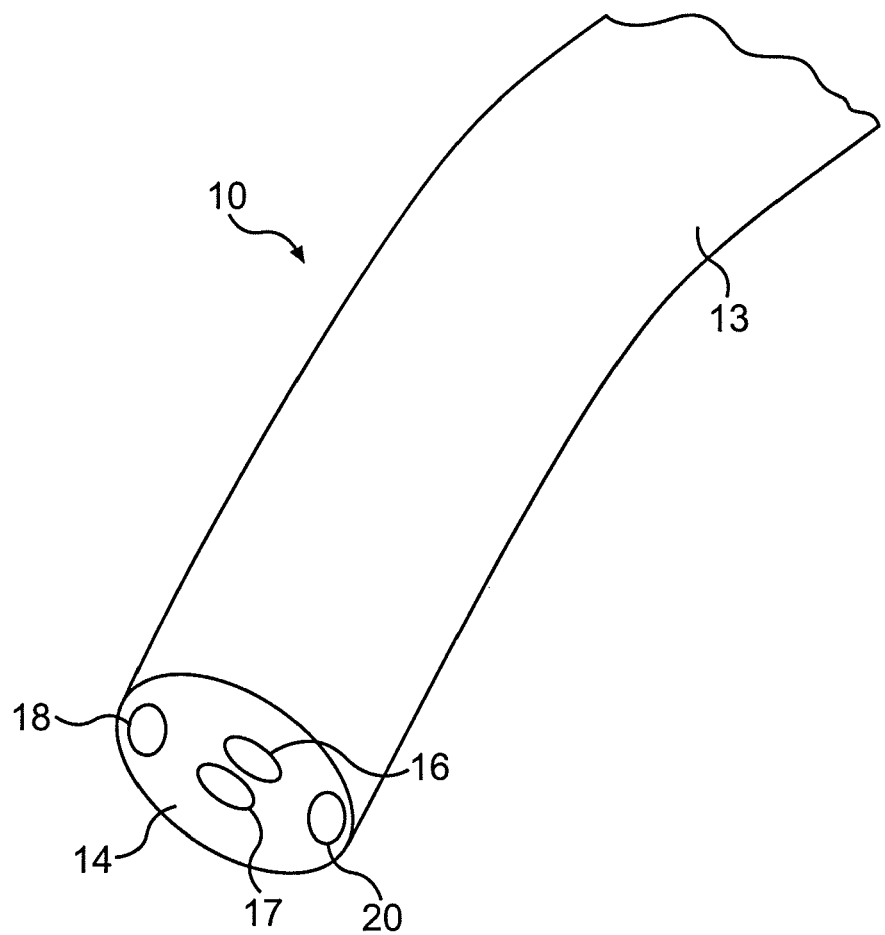
FIG. 1 is a fragmentary perspective view of a conventional endoscope.
Figure 2:
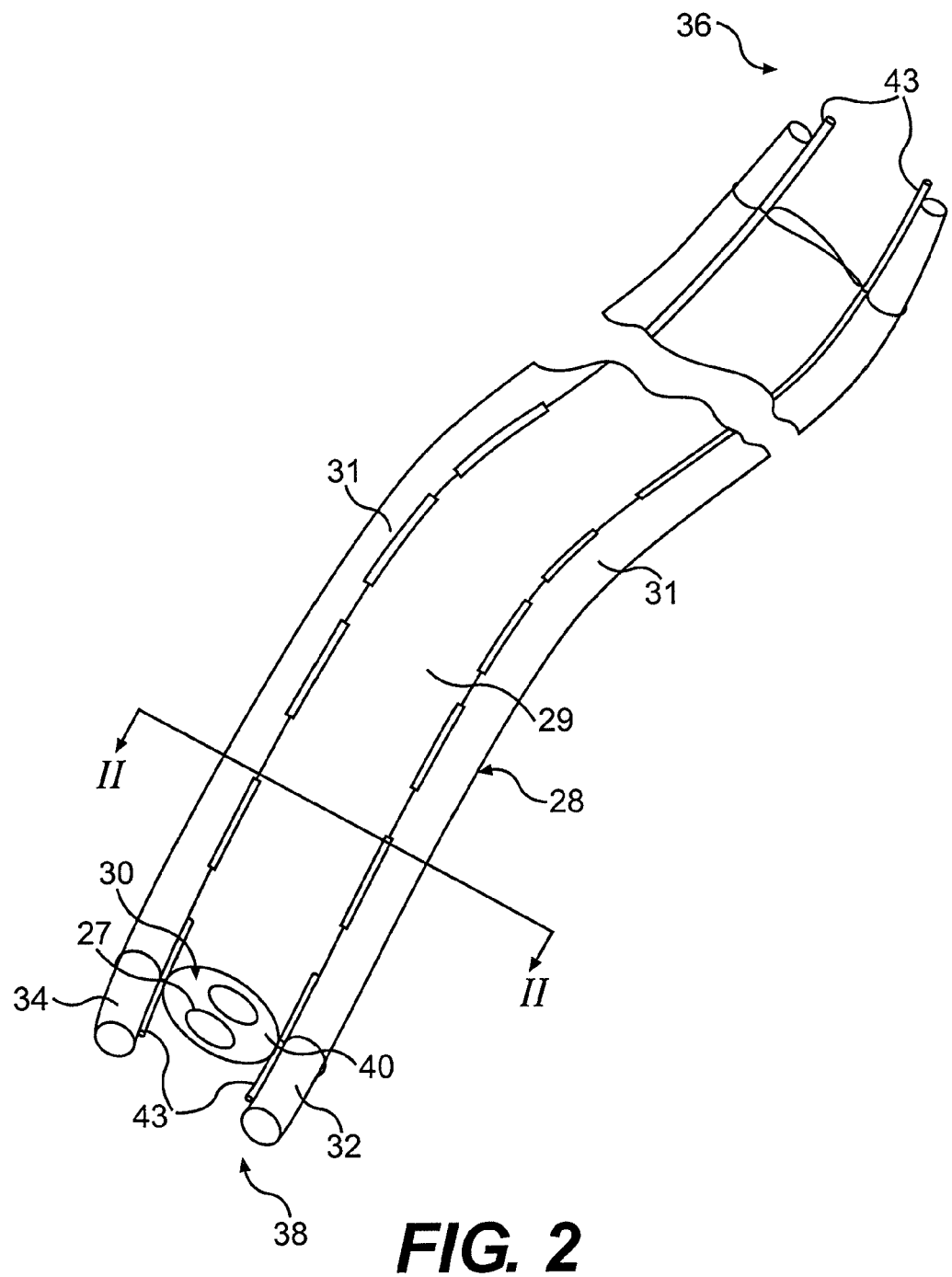
FIG. 2 is a fragmented perspective view of a preferred embodiment of a controllable endoscopic sheath according to the present invention.
Figure 3:
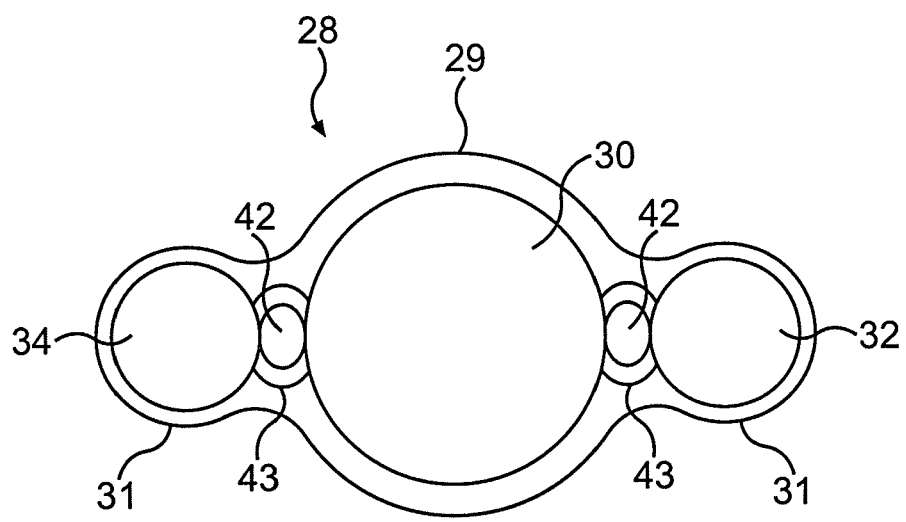
FIG. 3 is a cross-sectional view on line II-II of FIG. 2.

In a preferred embodiment of the present invention, as shown in FIGS. 2 and 3, a controllable endoscopic sheath 28 encloses an endoscope 30. Sheath 28 includes lumens 32, 34 extending from a proximal end 36 that exists external to endoscope 30 to a distal end 38. Sheath 28 also includes a central covering 29 that extends over the perimeter of endoscope 30 and is integral with slots 31 that cover lumens 32, 34. Coverings 29 and 31 and lumens 32, 34 are preferably made of a material suitable for insertion into a human body.

Not shown in the FIGS. 2 and 3 are many of the details of the proximal end of the complete endoscopic device, which includes endoscope 30 and sheath 28. For example, the proximal end of the endoscopic device includes a conventional endoscope proximal handle and is configured to receive the sheath of the present invention.

Lumens 32, 34 provide channels for the insertion of surgical instruments. The operator may control the movement of the surgical instruments at the distal end or operation site by manipulating a controlling device to be described. The controlled movement of the surgical instruments results from me controlled distal end deflection of the walls of the lumen.

The ability to deflect distal end 38 of the walls of lumen 32, 34 gives the operator increased control over the surgical instruments at the working area. Lumen 32, 34 is generally designed to accommodate medical instruments and are disposed at various locations about the perimeter of endoscope 30. Although the preferred embodiment shown in FIG. 2 includes two lumens 32, 34, it is to be understood that a controllable endoscopic sheath according to the present invention may include any number of lumens positioned around the perimeter of the endoscope. Preferably, the lumens are equally spaced about endoscope 30 to give the operator the greatest range of motion at the working area. For example, as depicted in FIG. 2, lumens 32, 34 are placed on opposing sides of the endoscope perimeter.

During insertion of the entire endoscopic device (endoscope 30 and sheath 28 including lumens 32, 34) into a patient, distal end 38 of the endoscopic device is generally flat. In other words, the distal ends of endoscope 30, and sheath 28, and its lumen 32, 34 terminate at substantially the same plane to enable the endoscopic device to navigate throughout the contours of the body cavity without causing unnecessary pain and discomfort to the patient. Although the insertion of the endoscopic device with one or more lumens 32, 34 extended is possible, it is not preferred because the extended lumens 32, 34 may block the visibility of viewing device 27 of endoscope 30 or collide with the side walls of the body cavity.

Once distal end 38 of the endoscopic device arrives at the desired surgical site, lumens 32, 34 are extended beyond endoscope tip 40 as desired by the operator. Although the lumens may extend simultaneously, preferably each lumen extends independently to offer the endoscope operator enhanced distal end control at the surgical site. As mentioned earlier, to permit the desired extension of lumens 32, 34 beyond endoscope tip 40, each lumen 32, 34 resides within a slot 31 of sheath 28, as best shown in FIG. 3. To aid in the movement of lumens 32, 34, the exterior surfaces of lumens 32, 34 and/or the interior surfaces of slots 31 preferably possess a lubricious coating or resin, such as teflon, polypropylene, or nylon. To move lumen 32, 34 with respect to endoscope tip 40, the operator advances or retracts lumen 32, 34 at the proximal end. This proximal end manipulation causes lumen 32, 34 to move within slots 31 of sheath 28. For example, to advance the distal end of a particular lumen 32, 34 beyond endoscope tip 40, the operator pushes the proximal end of the lumen 32, 34 towards the surgical site as desired. To retract the lumen 32, 34 from endoscope tip 40, the reverse procedure is implemented. Specific arrangements to advance and retract lumen 32, 34, and cause their deflection at the distal end, will be described herein.

By extending lumen 32, 34 beyond endoscope tip 40 and controlling its distal end deflection, the endoscope operator may manipulate the position of the surgical instruments at the operation site in a myriad of ways. This increased mobility and control optimizes the coverage area of the surgical instrument because lumens 32, 34 may extend beyond endoscope tip 40 and deflect in any direction desired by the operator. Further, the distal end extension of lumen 32, 34 beyond endoscope tip 40 provides the operator with enhanced control over the surgical instruments and the operation because lumen 32, 34 may transport the surgical instruments more closely to the operation site. For example, in certain cavities of the body, the contours of the operative channel may be such that the endoscopic device cannot traverse the operative channel. In such situations, the extension and control of lumen 32, 34 beyond endoscope tip 40 of endoscope 30 enables the operator to perform the surgical procedure in areas previously unreachable by conventional endoscopes.

The deflection of lumen 32, 34 at distal end 38 also allows for the interaction and communication between multiple surgical instruments. For example, one instrument may grasp and manipulate an object within the body cavity while the other instrument may perform the desired procedure. Since lumens 32, 34 are preferably dispersed on opposing ends of endoscope 30, the surgical instruments may communicate with each other at various angles previously unattainable using conventional endoscopes.

The present invention includes a device to control the deflection of the distal end of lumen 32, 34. The controller device, or actuator, according to a preferred embodiment and as depicted in FIGS. 2 and 3, includes wire member 42. Wire member 42 extends from the proximal end to the distal end of the endoscopic device and preferably extend along the walls of lumen 32, 34 and adjacent to endoscope 30. Wire member 42 has an elastic memory that aids in the deflection of the walls of lumen 32, 34. The elastic memory of wire member 42 is impeded by the rigidity of endoscope 30, and/or covering 29 and slots 31, such that the distal end of wire member 42 returns to its elastic memory only when extended beyond the distal end of endoscope 30, and/or covering 29 and slots 31. Preferably, wire member 42 is formed of nitinol, spring steel, or other suitable material of similar elastic characteristics. Wire member 42 is also preferably flat or oval shaped, however, other shaped structures are within the scope of the invention.

Wire member 42 is contained inside a tubular member 43 that extends along the outside of lumen 32, 34 and adjacent endoscope 30, as shown in FIG. 3. Tubular member 43 is fixedly disposed to the outside of lumens 32, 34 and extends from the proximal end to the distal end of the lumen. The distal end of tubular member 43 is sealed so that wire member 42 cannot extend beyond the confines of tubular member 43. The proximal end of tubular member 43, however, is open to permit the proximal end manipulation of wire member 42.

As previously discussed, at me time of endoscope insertion, the distal end of the endoscopic device remains substantially flat, i.e. in a single plane. Once arriving at the operation site, lumen 32, 34 is extended beyond endoscope tip 40. Once lumens 32, 34 are positioned, as desired, wire member 42 is advanced beyond endoscope tip 40 to create the desired distal end deflection. To move wire member 42 within tubular member 43, the operator advances or retracts wire member 42 at the proximal end. This proximal end manipulation causes wire member 42 to move in relation to tubular member 43. To enhance the movement of wire member 42 within tubular member 43, the interior of tubular member 43 preferably possesses a lubricious coating or resin, such as teflon, polypropylene, or nylon. As wire member 42 extends beyond endoscope tip 40, the distal end of wire member 42 returns to its elastic memory. This distal end deflection of wire member 42 causes tubular member 43 to deflect, which, in turn, causes deflection of the distal end of the lumen 32, 34 to which it connects. The endoscope operator may control the degree of distal end deflection of lumen 32, 34 by varying the distance that wire member 42 and/or lumen 32, 34 extend beyond endoscope tip 40.

Alternatively, wire member 42 may extend beyond endoscope tip 40 simultaneously with the advancement of lumen 32, 34. For example, wire member 42 may be fixedly fastened to the walls of lumen 32, 34 (without the provision of a tubular member) or may be fixedly fastened to tubular member 43 itself. In such cases, the distal end of wire member 42, as fixedly fastened proximate to the distal end of a lumen 32, 34, possesses no independent mobility, and the extension of wire member 42 beyond endoscope tip 40 depends upon the extension of its corresponding lumen 32, 34 beyond endoscope tip 40. To create the desired distal end deflection, lumens 32, 34 are extended beyond endoscope tip 40. As the distal end of lumen 32, 34 and wire member 42 protrude beyond endoscope tip 40, the distal end of wire member 42 extending beyond endoscope tip 40 returns to its natural deflected state due to its elastic memory. This deflection, in turn, causes lumen 32, 34 to deflect. To control the degree of distal end deflection of lumen 32, 34, the endoscope operator may vary the distance that lumen 32, 34 extend beyond endoscope tip 40.

Regardless of whether wire member 42 extends simultaneously with lumen 32, 34 or independently of lumen 32, 34, once wire member 42 extends beyond endoscope tip 40, wire member 42 returns to its naturally curved position. The distal end curvature of wire member 42 causes lumen 32, 34 to deflect. Because wire member 42 possesses an elastic memory with a stiffness insufficient to bend endoscope 30, wire member 42 returns to its elastic memory only after advancing beyond endoscope tip 40. Once wire member 42 extends beyond endoscope tip 40, the distal end of lumen 32, 34 deflects in response to the curvature of wire member 42.

Although the drawings depict only one wire member per lumen, multiple wire members may be used to controllably deflect a particular lumen. Additional wire members dispersed along the walls of the lumen offer enhanced control over the direction and deflection of the lumen. For example, by positioning the wire members along various points on the perimeter of the lumen, each wire member may control a different direction of deflection. The additional wire members, as positioned, give the operator the ability to deflect the distal end of the lumen in a multitude of directions.

Figure 4:
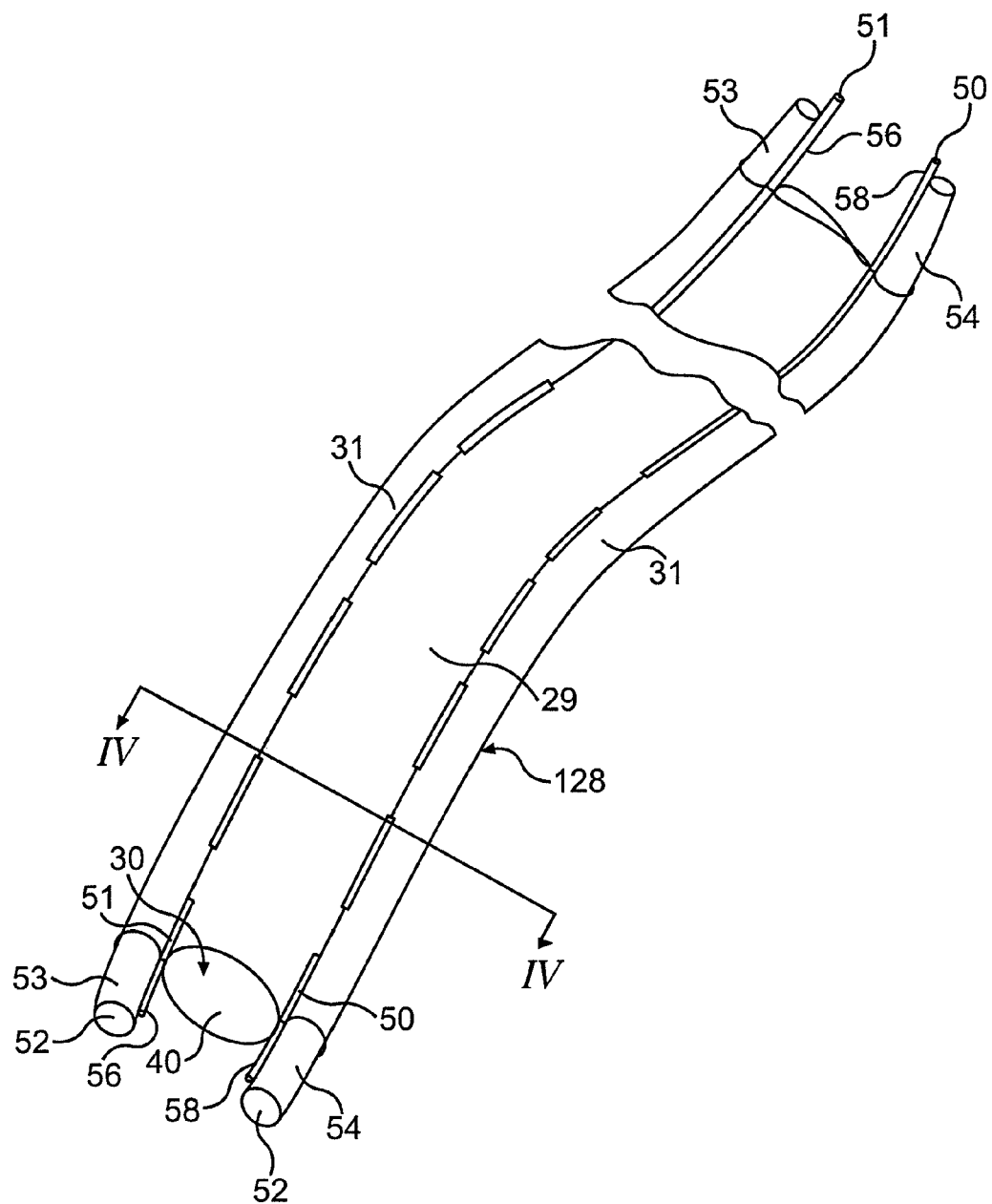
FIG. 4 is a fragmented perspective view of a second preferred embodiment of a controllable endoscopic sheath according to the present invention.
Figure 5:
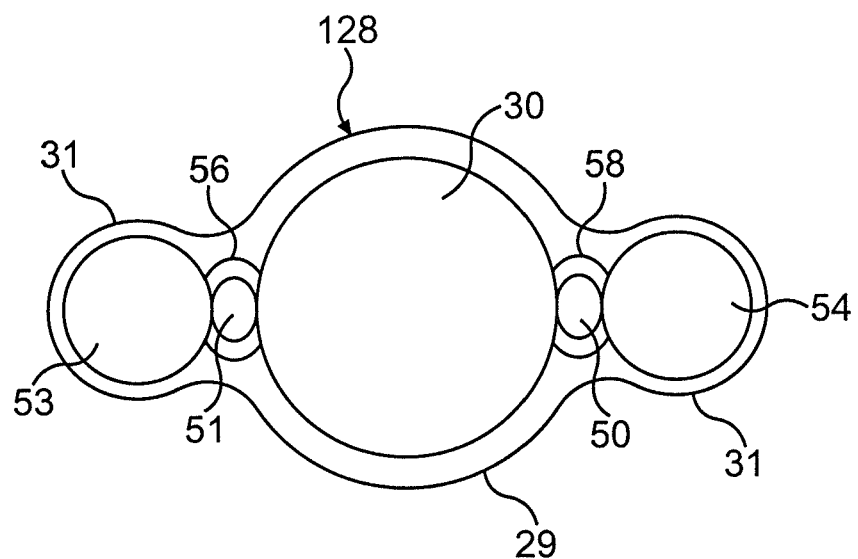
FIG. 5 is a cross-sectional view on line IV-IV of FIG. 4.

In a second preferred embodiment of the present invention, as shown in FIGS. 4 & 5, a controllable endoscopic sheath 128 includes an actuator having a stiffening member 50, 51. In addition, each lumen 53, 54 includes a deflectable lumen tip 52 having an elastic memory. Stiffening members 50, 51 extend from a proximal end to a distal end of endoscope 30 and possess distal end rigidity sufficient to impede only the elastic memory of lumen tip 52. Stiffening member 50, 51 may be formed of either silicon, urethane, expanded teflon, or other suitable material having sufficient rigidity.

Each stiffening member 50, 51 preferably resides inside a tubular member 56, 58 that is disposed along the outside of lumen 52, 54 and positioned adjacent to endoscope 30, as shown in FIG. 5. Tubular member 56, 58 is fixedly disposed to the outside of lumen 52, 54 and extends from the proximal end to the distal end of the lumen. The distal end of tubular member 56, 58 is sealed so that stiffening member 50, 51 cannot extend beyond the confines of tubular member 56, 58. The proximal end of tubular member 56, 58, however, is open to permit the proximal end manipulation of stiffening member 50, 51.

Similar to the previous embodiment, the endoscopic device enters and passes through a body cavity of the patient while the device has a substantially flat distal end. In other words, each of endoscope 30, sheath 128, and its lumen 53, 54 terminate at about the same distal plane. As configured, the endoscopic device traverses the body cavity until the distal end of endoscope 30 arrives at the operation site. To create the desired distal end deflection, lumens 53, 54 are first extended beyond endoscope tip 40. Once beyond endoscope tip 40, the elastic memory of tip 52 of lumen 53, 54 causes the distal end of lumen 53, 54 to deflect to their natural deflected state. To impede this deflection and control the curvature of the distal end of lumen 53, 54, stiffening member 50, 51 is extended within tubular members 56, 58 to a point beyond endoscope tip 40. The operator may control the degree of distal end deflection of lumen 53, 54 by varying the distance that the lumen 53, 54 and/or stiffening member 50, 51 extends beyond endoscope tip 40.

To move stiffening member 50, 51 within tubular member 56, 58, the operator advances or retracts stiffening member 50, 51 at the proximal end. This proximal end manipulation causes stiffening member 50, 51 to move in relation to tubular member 56, 58. To enhance the movement of stiffening member 50, 51, the interior of tubular member 56, 58 preferably possesses a lubricious coating or resin, such as teflon, polypropylene, or nylon. As a stiffening member 50, 51 extends beyond endoscope tip 40, the distal end of stiffening member 50, 51 impedes the deflection of tip 52 of the corresponding lumen 53, 54.

Accordingly, the amount of lumen deflection can be controlled by limiting the deflection of tip 52 of lumen 53, 54 by extending stiffening member 50, 51 beyond endoscope tip 40. In contrast to the first embodiment, where advancement of wire member 42 enhances the distal end deflection, advancing stiffening member 50, 51 beyond endoscope tip 40 hinders the elastic deflection of tip 52, thus, limiting the deflection of lumen 53, 54.

Although the drawings depict only one stiffening member per lumen, multiple stiffening members may be used to controllably deflect a particular lumen. Additional stiffening members dispersed along the walls of the lumen offer enhanced control over the direction and deflection of the lumen. For example, by positioning the stiffening members along various points on the perimeter of the lumen, each stiffening member may control a different direction of deflection. The additional stiffening members, as positioned, give the operator the ability to deflect the distal end of the lumen in a multitude of directions.

In a variation of the second preferred embodiment, a stiffening member may be fixedly disposed to the outside of endoscope 30 and adjacent to lumen 53, 54. As disposed, the distal end of the stiffening member extends along the distal end of endoscope 30 and possesses sufficient rigidity to impede the elastic memory of lumen tip 52. To create the desired distal end deflection, lumens 53, 54 are extended beyond endoscope tip 40, as previously described. As the distal end of lumen 53, 54 extends beyond endoscope top 40, the elastic memory of tip 52 causes the distal end of lumen 53, 54 to deflect. To control the degree of distal end deflection of lumen 53, 54, the endoscope operator may vary the distance lumen 53, 54 extends beyond endoscope tip 40 by manipulating the proximal end of lumen 53, 54.

Figure 6:
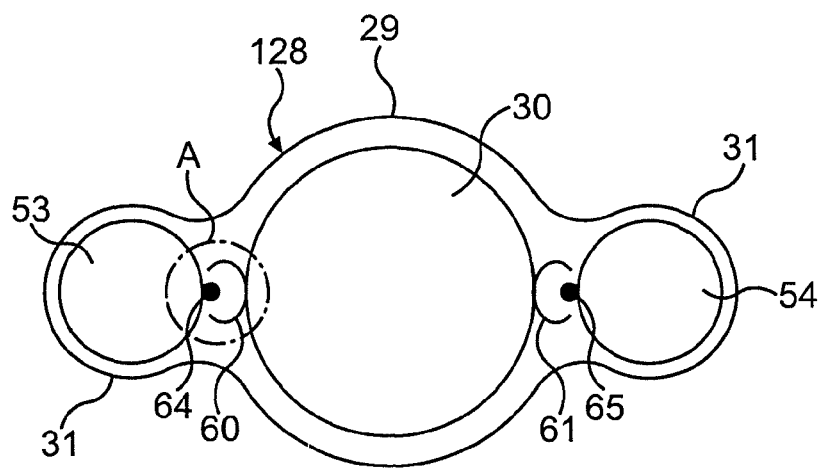
FIG. 6 is a cross-sectional view similar to FIG. 5, but showing a variation of the second embodiment.
Figure 6A:
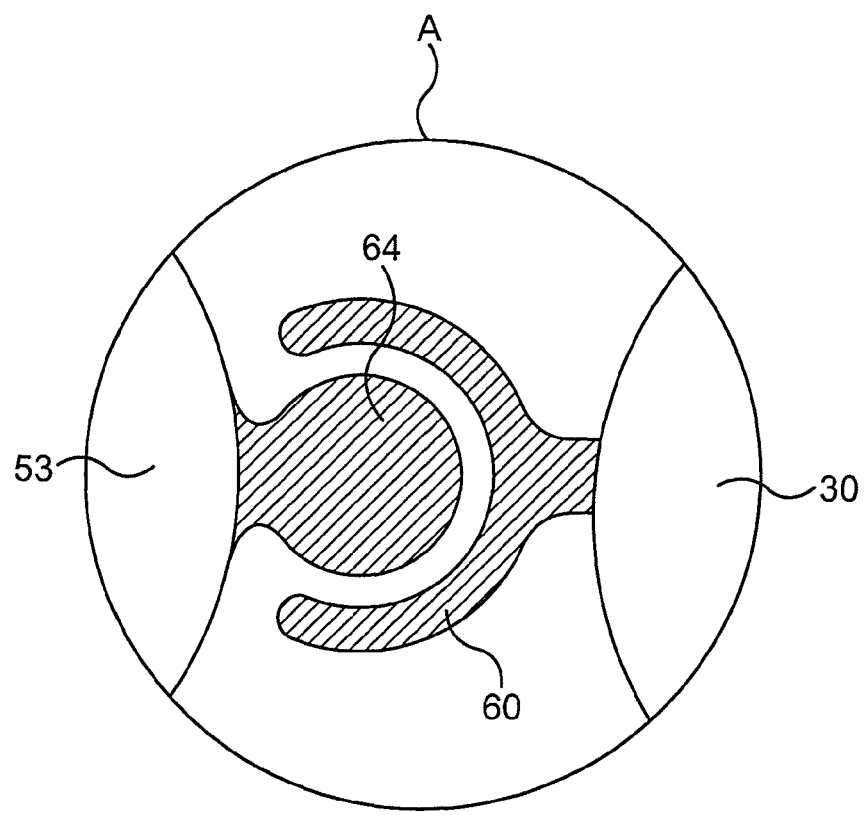
FIG. 6A is an exploded cross-sectional view of region A of FIG. 6.

As an example of this variation of the second embodiment and as shown in FIGS. 6 and 6A, a stiffening member may include sheath guide 60, 61 fixedly disposed to the outside of endoscope 30 and adjacent to lumen 53, 54. As best shown in FIG. 6A, sheath guide 60, 61 is configured to engage with guide pin 64, 65. Guide pin 64, 65 is fixedly disposed along the walls of lumen 53, 54 and adjacent to endoscope 30. Once again, the distal end of sheath guide 60, 61 possesses sufficient rigidity to impede the deflection of the distal end of lumen 53, 54.

To create the desired distal end deflection, lumen 53, 54 extends beyond endoscope tip 40, as previously described. As the distal end of lumen 53, 54 extends beyond endoscope tip 40, the distal end of guide pin 64, 65 no longer communicates with sheath guide 60, 61. As such, the deflection of tip 52 due to its elastic memory is no longer impeded by sheath guide 60, 61, and the distal end of lumen 53, 54 elastically deflects. Accordingly, the endoscope operator may control the degree of distal end deflection of lumen 53, 54 by regulating how far the distal end of guide pin 64, 65 (and lumen 53, 54 to which it is attached) extends beyond endoscope tip 40 and sheath guide 60, 61.

In a third preferred embodiment of the present invention, a controllable endoscopic sheath 228 includes an actuator having a flexible extension. The flexible extension eccentrically attaches to a flexible elongated member. This third embodiment of an endoscopic sheath according to the present invention is illustrated in FIGS. 7-12. Preferably, the flexible elongated member includes cable 70, 72, the flexible extension includes spherical mating members 74, 76, 78, and sheath 228 includes an outer sheath 82 and a inner sheath 80. Spherical members 74, 76, 78 are preferably constructed of a stainless steel or plastic material.

Figure 9:
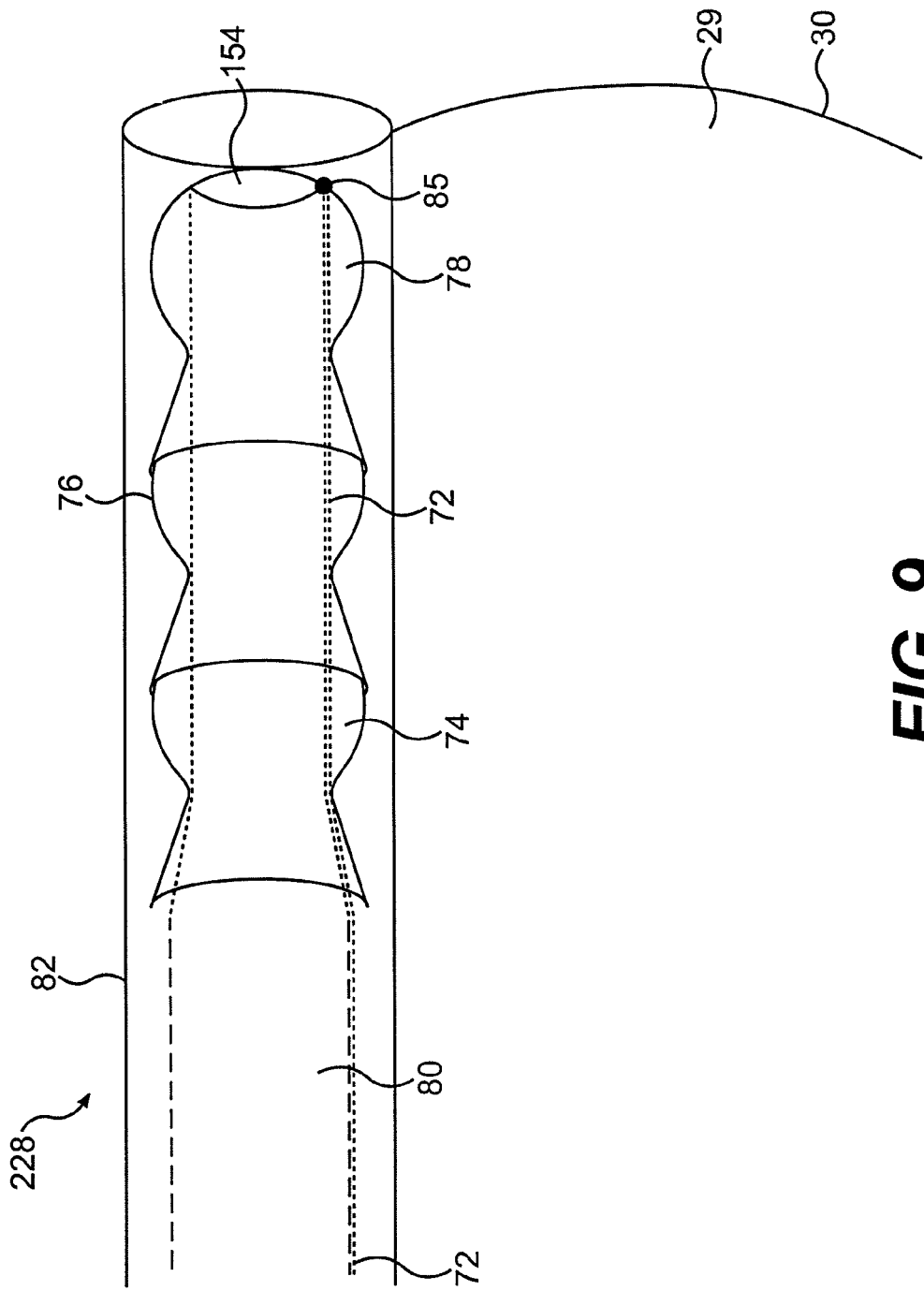
FIG. 9 is a cross-sectional view on line VIII-VIII of FIG. 7.
Figure 10:
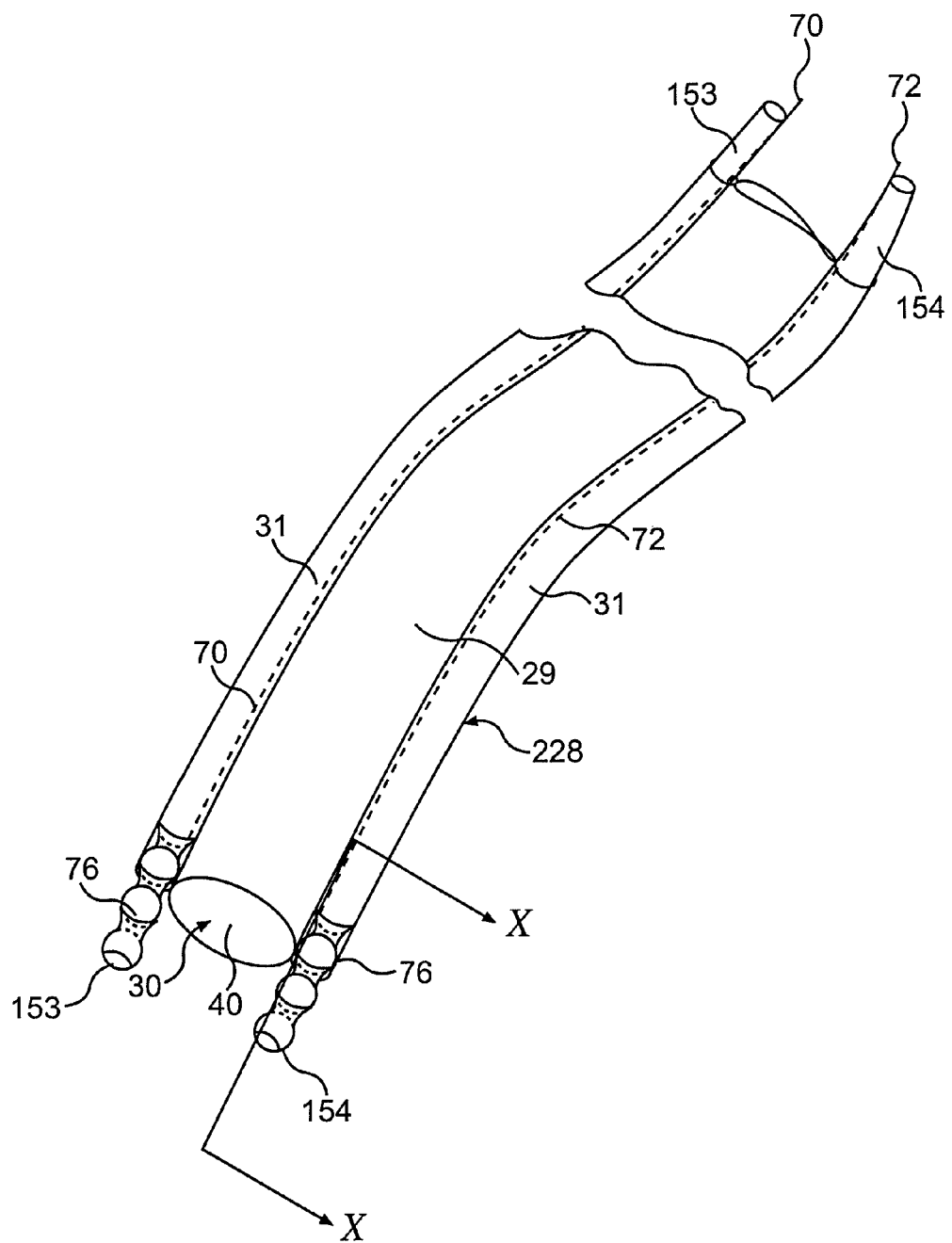
FIG. 10 is a fragmented perspective view of the third preferred embodiment showing the extension of lumens beyond an endoscopic distal tip.

Each cable 70, 72 extends from the proximal end of its corresponding lumen 153, 154 to the distal end, where it eccentrically extends along corresponding spherical mating members 74, 76, 78 positioned at the distal end of lumen 153, 154. As illustrated in FIG. 9, preferably, cable 72 eccentrically extends through each of the spherical mating members 74, 76, 78, but cable 72 may alternatively traverse along the exterior of each of spherical mating members 74, 76, 78.

Figure 11:
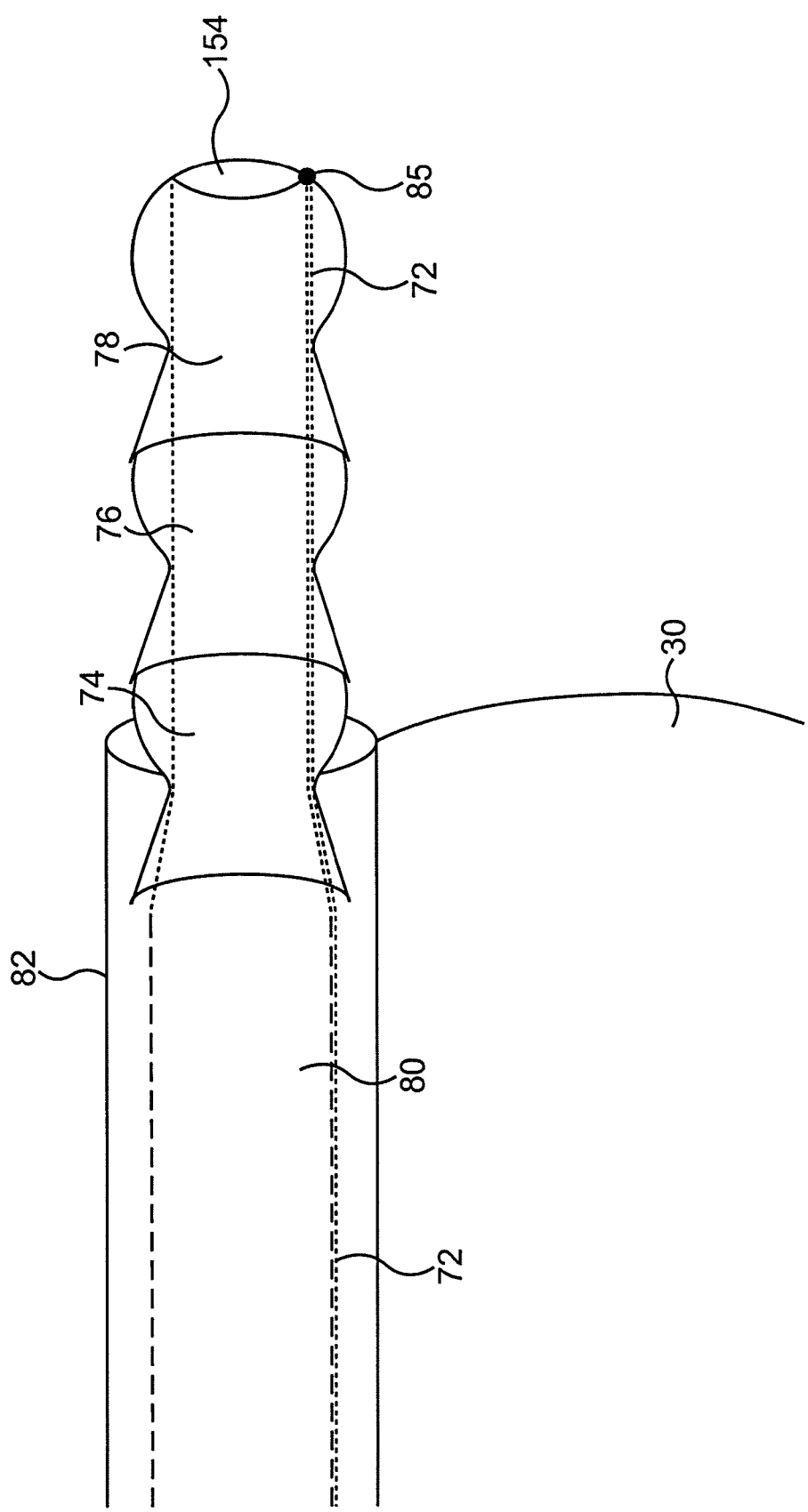
FIG. 11 is a cross-sectional view on line X-X of FIG. 10.
Figure 12:
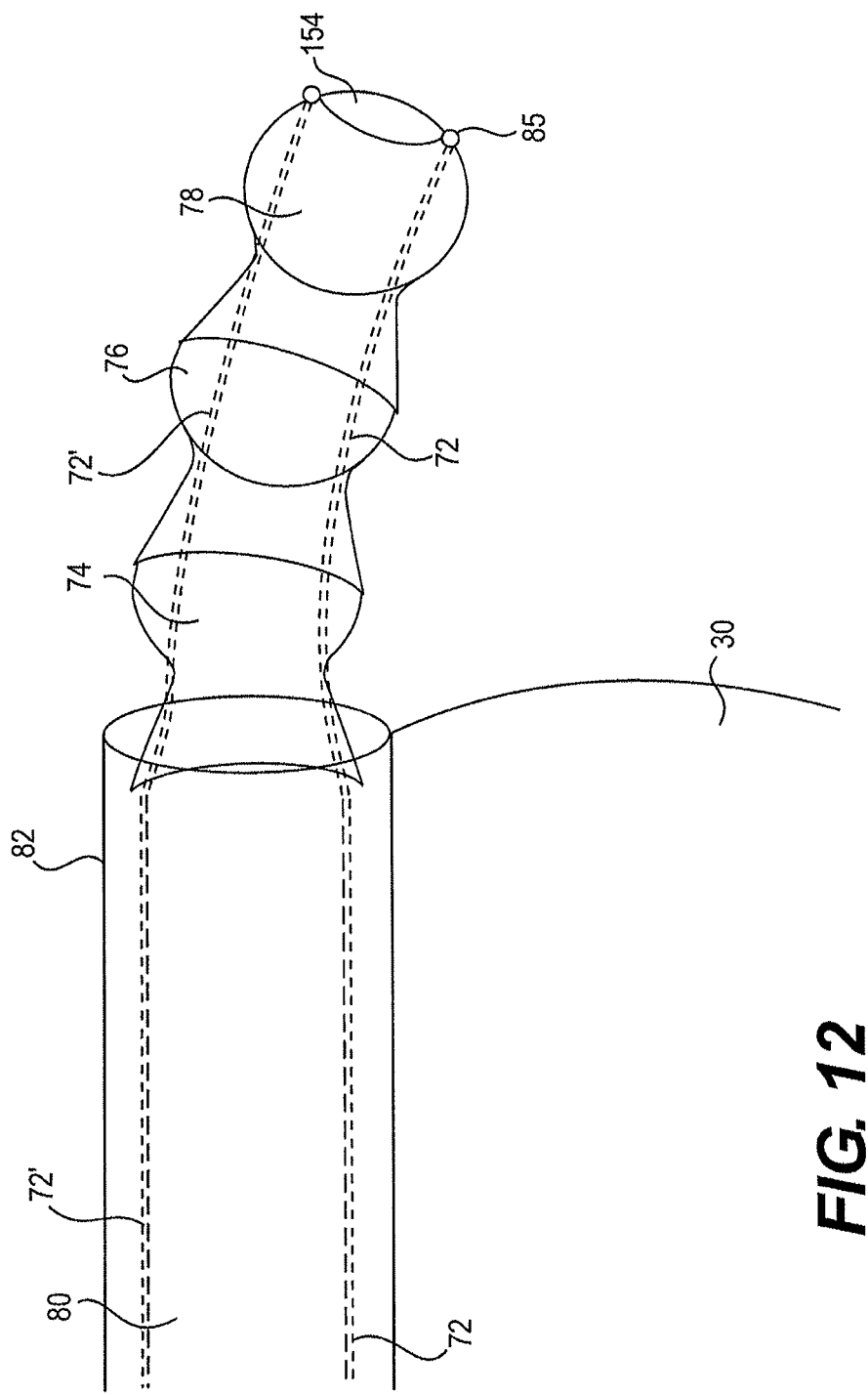
FIG. 12 is a cross-sectional view on line X-X of FIG. 10 showing the distal end deflection of the lumens.

To prevent the distal end of cable 72 from proximally retracting beyond the distal-most spherical mating member 78, the distal end of cable 72 includes a stop 85, as shown in FIGS. 9, 11, and 12. Stop 85 may be a sphere, or similar structure, having a surface area larger than that of the passage traversed by cable 72. As configured, stop 85 impedes the proximal retraction of cable 72 beyond the most distal end spherical mating member 78, because stop 85 restrictively engages the distal end of the cable passage.

Preferably, stop 85 securely fastens to the distal end of cable 72. For example, stop 85 may include a hollow interior that serves as a channel for receiving the distal end of cable 72. As configured, the exterior of the distal end of cable 72 and the interior of stop 85 include complementary threaded surfaces that permit the secure fastening of stop 85 on the distal end of cable 72. Alternatively, cable 72 may be constructed to permanently include at its distal end stop 85. Regardless of the particular construction, stop 85 impedes the proximal retraction of cable 72 beyond the most distal end spherical mating member 78.

Figure 15:
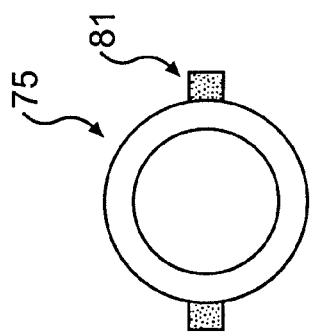
FIG. 15. is an end view of a male end of the spherical mating member of FIG. 13.
Figure 14:
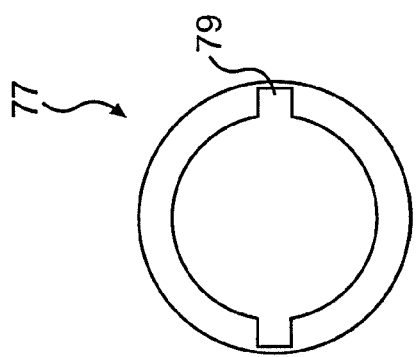
FIG. 14. is an end view of a female receiving end of the spherical mating member of FIG. 13.

As depicted in FIGS. 9, 11, and 12, spherical mating members 74, 76, 78 preferably reside within the interior distal portion of outer sheath 82. As disposed, spherical mating members 74, 76, 78 encompass and define the distal end portion of lumen 153, 154, while the remaining portion of lumen 153, 154 is encompassed and defined by inner sheath 80, which extends from the proximal end of lumen 153, 154 to a point proximate to the distal end of lumen 153, 154. The distal end of inner sheath 80 attaches to the most proximal spherical mating member 74 to ensure the continuity of lumen 153, 154 from the proximal end to the distal end of outer sheath 82. To permit the travel of surgical instruments through the distal end of lumen 153, 154, spherical mating members 74, 76, 78 include a hollow center passage 89 (see FIGS. 13-15) substantially equal to the inner surface dimensions of inner sheath 80. Accordingly, the working channel of lumen 153, 154 is defined by the inner surface dimensions of inner sheath 80 and center passage 89 of spherical mating members 74, 76, 78. To ensure the unhampered unobstructed passage of surgical instruments, spherical mating members 74, 76, 78 are preferably constructed of a stainless steel or plastic material.

Figure 13:
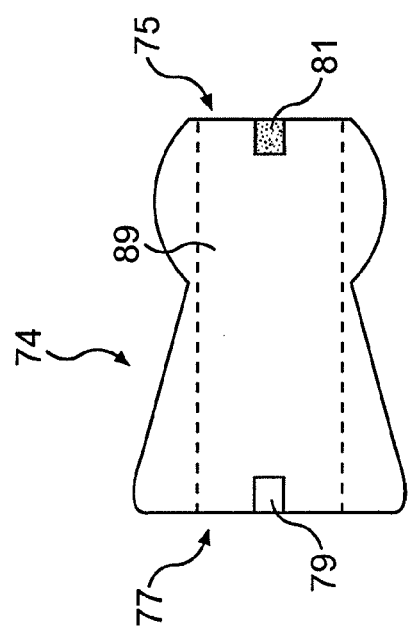
FIG. 13 is a side view of a spherical mating member as incorporated in the third preferred embodiment of a controllable endoscopic sheath according to the present invention.

As illustrated in FIG. 13, each of spherical mating members 74, 76, 78 includes a male end 75 and a female receiving end 77. Male end 75 and female receiving end 77 complement one another in configuration. In particular, the outer surface dimensions of male end 75 closely correspond to the inner surface dimensions of female receiving end 77. As depicted in FIG. 13, end 75 includes a spherical shape of a diameter complimentary in size to the cone shaped opening of receiving end 77. This complementary configuration facilitates a secure attachment between respective male end 75 and female receiving end 77 of adjoining spherical mating members 74, 76, 78. To attach the respective ends of the spherical mating members, end 75 is forced into receiving end 77. The amount of outer surface area of end 75 encompassed by the interior of receiving end 77 depends upon the amount of force used in inserting end 75 into receiving end 77. Typically, the greater the force, the more receiving end 77 encompasses end 75, and vice versa. Once attached, to prevent adjoining spherical mating members 74, 76, 78 from uncontrollably separating from one another, female receiving end 77 includes a rounded end 99 that encircles a portion of attached male end 75.

Preferably, each of spherical mating members 74, 76, 78 also includes a slot 79 and an index tab 81. Slot 79 is disposed at female receiving end 77, while index tab 81 is disposed at male end 75. The interaction between slot 79 and index tab 81 enhances the attachment between the spherical mating members and controls the flexibility of the adjoining spherical mating members 74, 76, 78. As end 75 is inserted into receiving end 77, slot 79 and index tab 81 are aligned so that slot 79 may receive index tab 81. Depending upon the force exerted in attaching end 75 into receiving end 77, index tab 81 may rest within slot 89 at an increased or decreased dept.

The degree of deflection of the adjoining spherical members is directly dependent upon the depth of index tab 81 in slot 79. For example, allowing index tab 81 to travel an increased slot depth allows end 75 to delve deeper into receiving end 77, thus, providing adjoining spherical mating members 74, 76, 78 with increased flexibility. Alternatively, a decreased slot depth limits the penetration of male end 75 into female receiving end 77, therefore, limiting the degree of deflection of adjoining spherical mating members 74, 76, 78. Depending upon the requirements of the particular endoscopic procedure, the design of the spherical mating members permits the endoscope operator to vary its flexibility accordingly by altering the depth of index tab 81 in slot 79.

FIG. 9 shows features of the distal end of lumen 154 and corresponding structure. Preferably, lumen 153 and corresponding structural elements are similarly arranged. As illustrated in FIG. 9, lumen 154, spherical mating members 74, 76, 78, and cable 72 preferably exist in two separate sheaths. The first sheath, an inner sheath 80, extends from the proximal end of the endoscope to a point proximate to the distal end of the endoscope. The distal end of inner sheath 80 terminates at spherical mating members 74, 76, 78 and preferably attaches to the most proximal end spherical member 74. Lumen 154 is therefore defined by the interior of inner sheath 80 and central passage 89 of spherical mating members 74, 76, 78. The proximal and distal ends of inner sheath 80 and central passages 89 are open to permit the unimpeded movement of surgical instruments through the interior of lumen 154.

As illustrated in FIG. 9, cable 72 preferably extends along the exterior of inner sheath 80. Cable 72, however, may also extend within the walls of inner sheath 80 or along the interior of sheath 80. The second sheath, an outer sheath 82, houses spherical mating members 74, 76, 78, cable 72, inner sheath 80, and lumen 154. Outer sheath 82 is fixedly disposed along the exterior of endoscope 30 and extends from the proximal end to the distal end of endoscope 30. As disposed, outer sheath 82 acts as a slot of sheath 228 in that it permits the movement of inner sheath 80, spherical members 74, 76, 78, cable 72, and lumen 154 in relation to endoscope 30. The distal end of outer sheath 82 is open to permit inner sheath 80, spherical members 74, 76, 78, cable 72, and lumen 154 to extend beyond endoscope tip 40. The proximal end of outer sheath 82 is similarly open to permit the proximal end manipulation of cable 72 and inner sheath 80.

Figure 7:
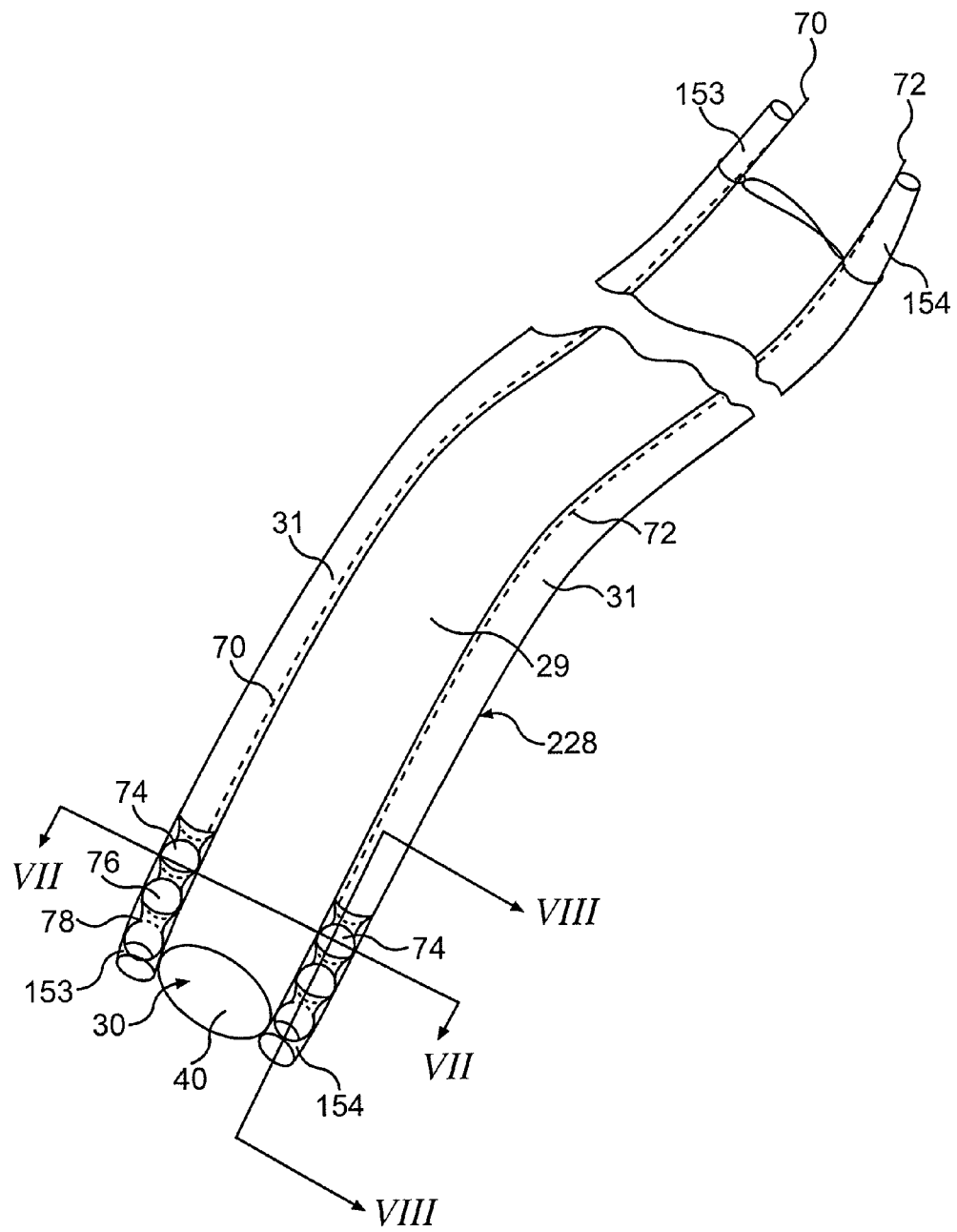
FIG. 7 is a fragmented perspective view of a third preferred embodiment of a controllable endoscopic sheath according to the present invention.
Figure 8:
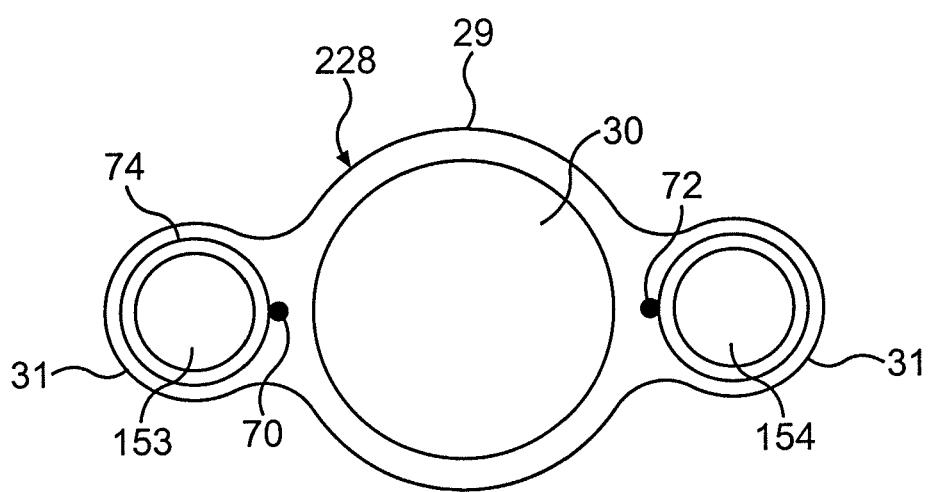
FIG. 8 is a cross-sectional view on line VII-VII of FIG. 7.

Similar to the previous embodiments and as depicted in FIGS. 7 and 9, the endoscopic device traverses the cavities of the body with a substantially flat distal end, where each of the endoscope and sheath, with its lumens, distally terminate at about the same plane. Once arriving at the operation site, the endoscope operator extends one or more lumens 153, 154 beyond endoscope tip 40 and proximate to the operation site by manipulating the proximal end of the endoscopic device.

To extend lumen 153, 154, the proximal end of inner sheath 80 is advanced by the endoscope operator towards the operation site. To enhance the movement of inner sheath 80 within outer sheath 82, the interior of outer sheath 82 and/or the exterior of inner sheath 80 are preferably composed of a lubricious material, such as teflon, polypropylene, or nylon. Because lumen 153, 154 is defined by the interior of inner sheath 80 and attached central passage 89, the proximal end movement of inner sheath 80 corresponds to a similar distal end movement of lumen 153, 154. As mentioned, the distal end of inner sheath 80 terminates at and is attached to the most proximal end spherical mating member 74. Thus, as the proximal end of inner sheath 80 is advanced towards the operation site, the distal end of inner sheath 80 similarly advances spherical mating members 74, 76, 78. The advancement of spherical mating members 74, 76, 78 as well as the attachment of the most proximal end spherical member to the distal end of lumen 154 ensure a distal advancement of inner sheath 80 that corresponds to the proximal advancement of inner sheath 80.

After lumen 153, 154 is advanced, as desired, the endoscope operator manipulates the proximal end of cable 70, 72 to create the necessary distal end deflection of lumen 153, 154. At the time of insertion, spherical mating members 74, 76, 78 are loosely oriented with respect to one another, as shown in FIG. 9. In other words, the distal end of cable 70, 72 provides insufficient tension to cause spherical mating members 74, 76, 78 to forcefully abut. As the endoscope operator retracts the proximal end of cables 70, 72, the corresponding length of cable 70, 72 connected to spherical mating members 74, 76, 78 shortens. The shortening of this cable length causes the distal end of cable 70, 72 to proximally retract along spherical mating members 74, 76, 78 until stop 85 engages the most distal end spherical mating member 74. At this particular point, the tension in cable 70, 72 causes spherical mating members 74, 76, 78 to forcefully abut one another. Because spherical mating members 74, 76, 78 are tightly aligned with respect to one another and stop 85 prevents cable 72 from retracting through spherical members 74, continual proximal end retraction of cable 72 causes a bend in the alignment of spherical members 74, 76, 78, as shown in FIG. 12. The distal end of lumen 154, which corresponds to central passage 89 of spherical members 74, 76, 78, deflects in response to the bent alignment of the spherical mating members. To control the amount of distal end deflection of lumens 153, 154, the endoscope operator may vary the retraction of cable 70, 72 in the proximate direction to control amount of bend imposed on spherical mating members 74, 76, 78.

Although the drawings depict only one cable and three spherical members per lumen, additional cables 72' may be eccentrically positioned along the respective spherical members to offer enhanced control over the direction of the distal end deflection of the lumen. These additional cables 72' give the operator the ability to deflect the distal end of the lumen in a multitude of directions, because each cable, as eccentrically positioned along the spherical members, may control a different direction of deflection. In addition, more or less than three spherical members may be used to provide more or less precision in the degree of distal end deflection of the lumen.

It will be apparent to those skilled in the art that various modifications and variations can be made in the endoscopic device of the present invention and in construction of this endoscopic device without departing from the scope or spirit of the invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical device, comprising:
   an elongate body having a longitudinal axis and a distal end;
   a channel at least partially extending through the body and configured to receive a viewing device, wherein the viewing device is moveable relative to the body along the longitudinal axis of the body;
   a flexible lumen extending distally from the distal end of the body, and including a distal end and a plurality of articulating members, wherein each articulating member is differently located along a longitudinal axis of the flexible lumen and is moveably coupled to an adjacent articulating member to permit deflection of the distal end of the flexible lumen; and
   an elongate control member having a distal part fixed to a distal portion of the flexible lumen and having a proximal part moveable relative to a proximal portion of the flexible lumen to control deflection of the flexible lumen.

2. The medical device of claim 1, wherein the flexible lumen includes a passage configured to receive a surgical instrument.

3. The medical device of claim 2, wherein each articulating member includes a passageway extending therethrough and forming part of the passage.

4. The medical device of claim 1, wherein the flexible lumen is moveable relative to the body along the longitudinal axis of the body.

5. The medical device of claim 1, wherein the elongate control member resides within the flexible lumen.

6. The medical device of claim 1, wherein the elongate control member includes a distally located stop.

7. The medical device of claim 1, further including a second elongate control member moveable relative to the flexible lumen, wherein the elongate control member controls deflection of the flexible lumen in a first direction and the second elongate control member controls deflection of the flexible lumen in a second direction different to the first direction.

8. The medical device of claim 1, wherein each of the plurality of articulating members is configured to rotate relative to an adjacent articulating member.

9. The medical device of claim 1, wherein at least one of the plurality of articulating members is coupled to the elongate control member.

10. The medical device of claim 1, wherein at least one of the plurality of articulating members includes a curved surface configured to moveably couple to a corresponding curved surface of the adjacent articulating member.

11. The medical device of claim 1, wherein at least one of the plurality of articulating members includes a distal end configured to engage a proximal end of the adjacent articulating member.

12. The medical device of claim 1, wherein at least one of the plurality of articulating members includes a tab configured to engage a slot located on the adjacent articulating member.

13. The medical device of claim 1, wherein the plurality of articulating members are located distally along the flexible lumen.

14. The medical device of claim 13, wherein the flexible lumen includes a proximal section constructed of plastic material.

15. The medical system of claim 1, wherein the elongate control member is moveably coupled to a first articulating member and fixedly coupled to a second articulating member different to the first articulating member.

16. The medical system of claim 1, wherein the plurality of articulating members includes a proximal-most articulating member, a distal-most articulating member, and at least one articulating member located distal to the proximal-most articulating member and proximal to the distal-most articulating member.

17. The medical device of claim 1, wherein the proximal part of the elongate control member is located proximal to a proximal region of the body and is configured to move relative to the proximal region of the body to transfer a tension applied to the proximal part of the elongate control member to the distal part of the elongate control member to control deflection of the flexible lumen.

18. A medical device, comprising:
an elongate body having a longitudinal axis, a distal end, and a proximal end;
a channel extending from the proximal end and at least partially through the body, wherein the channel is configured to receive a viewing device;
a first flexible lumen extending from the distal end of the body, having a first passage, and having a first distal section located distal to the distal end of the body, wherein the first distal section includes a plurality of first articulating members, each first articulating member having a first passageway extending therethrough and forming part of the first passage;
a first elongate control member having a distal part fixedly coupled to the first distal section, extending from the first distal section to at least a proximal region of the body, and being moveable relative to the first distal section to control movement of the first distal section;
a second flexible lumen extending from the distal end of the body, having a second passage, and having a second distal section located distal to the distal end of the body, wherein the second distal section includes a plurality of second articulating members, each second articulating member having a second passageway extending therethrough and forming part of the second passage; and
a second elongate control member coupled to the second distal section and moveable relative to the second distal section to control movement of the second distal section.

19. The medical device of claim 18, wherein the first flexible lumen and the second flexible lumen are located on generally opposite sides of the longitudinal axis of the body.

20. The medical device of claim 18, wherein the first distal section is moveable relative to the body, and the second distal section is moveable relative to the body separate from movement of the first distal section.

21. The medical device of claim 18, wherein the first elongate control member extends generally from the first distal section to at least the proximal end of the body.

22. A medical system, comprising:
an endoscope;
an elongate body configured to at least partially surround the endoscope, wherein the body has a longitudinal axis and a distal end;
a flexible lumen extending distally from the distal end of the body and having a distal section located distal to the distal end of the body, wherein the distal section includes a plurality of articulating members, and each articulating member is located at a different position along a longitudinal axis of the distal section and moveably coupled to an adjacent articulating member to permit deflection of the distal section; and
an elongate control member moveable relative to a proximal section of the flexible lumen to control deflection of the distal end of the flexible lumen when the distal section of the flexible lumen is located distal to the distal end of the body, wherein the elongate control member is fixedly coupled to at least one of the plurality of articulating members.

23. The medical system of claim 22, further including a surgical instrument configured to reside at least partially within a lumen of the flexible lumen.

24. The medical system of claim 22, wherein the endoscope is moveable relative to the elongate body.

* * * * *